US012690582B2

(12) United States Patent
Zacharias et al.

(10) Patent No.: US 12,690,582 B2
(45) Date of Patent: Jul. 28, 2026

(54) VIABLE CELL COMPOSITIONS, AND METHODS RELATED TO SAME

(71) Applicant: Gallant Pet, Inc., San Diego, CA (US)

(72) Inventors: Shelly J. Zacharias, Indianapolis, IN (US); Erik J. Woods, Indianapolis, IN (US)

(73) Assignee: Gallant Pet, Inc.

( * ) Notice: Subject to any disclaimer, the term of this patent is extended or adjusted under 35 U.S.C. 154(b) by 0 days.

(21) Appl. No.: 16/738,870

(22) Filed: Jan. 9, 2020

(65) Prior Publication Data

US 2020/0383317 A1      Dec. 10, 2020

Related U.S. Application Data

(63) Continuation of application No. 15/471,578, filed on Mar. 28, 2017, now abandoned.

(60) Provisional application No. 62/314,316, filed on Mar. 28, 2016.

(51) Int. Cl.
| | |
|---|---|
| *A01N 1/126* | (2025.01) |
| *A01N 1/125* | (2025.01) |
| *A61K 35/28* | (2015.01) |

(52) U.S. Cl.
CPC ............. *A01N 1/126* (2025.01); *A01N 1/125* (2025.01); *A61K 35/28* (2013.01)

(58) Field of Classification Search
CPC ..... A01N 1/0226; A01N 1/0221; A61K 35/28
USPC ...................................................... 424/93.7
See application file for complete search history.

(56) References Cited

U.S. PATENT DOCUMENTS

| | | |
|---|---|---|
| 3,753,432 A | 8/1973 | Guerra |
| 3,858,571 A | 1/1975 | Rudolph |
| 3,995,772 A | 12/1976 | Liautaud |
| 4,004,975 A | 1/1977 | Lionetti et al. |
| 4,292,972 A | 10/1981 | Pawelchak et al. |
| 4,347,234 A | 8/1982 | Wahlig et al. |
| 4,376,634 A | 3/1983 | Prior et al. |
| 4,404,970 A | 9/1983 | Sawyer |
| 4,412,947 A | 11/1983 | Cioca |
| 4,512,342 A | 4/1985 | Zaneveld et al. |
| 4,606,337 A | 8/1986 | Zimmermann et al. |
| 4,616,998 A | 10/1986 | Wong |
| 4,705,517 A | 11/1987 | DiPisa, Jr. |
| 4,852,568 A | 8/1989 | Kensey |
| 4,890,612 A | 1/1990 | Kensey |
| 4,948,540 A | 8/1990 | Nigam |
| 4,981,465 A | 1/1991 | Ballan et al. |
| 5,021,059 A | 6/1991 | Kensey et al. |
| 5,061,274 A | 10/1991 | Kensey |
| 5,192,302 A | 3/1993 | Kensey et al. |
| 5,222,974 A | 6/1993 | Kensey et al. |
| 5,224,493 A | 7/1993 | Sawan et al. |
| 5,268,148 A | 12/1993 | Seymour |

| | | |
|---|---|---|
| 5,282,827 A | 2/1994 | Kensey et al. |
| 5,310,407 A | 5/1994 | Casale |
| 5,334,216 A | 8/1994 | Vidal et al. |
| 5,360,410 A | 11/1994 | Wacks |
| 5,374,261 A | 12/1994 | Yoon |
| 5,382,261 A | 1/1995 | Palmaz |
| 5,383,886 A | 1/1995 | Kensey et al. |
| RE34,866 E | 2/1995 | Kensey et al. |
| 5,388,588 A | 2/1995 | Nabai et al. |
| 5,391,183 A | 2/1995 | Jansen et al. |
| 5,437,631 A | 8/1995 | Jansen |
| 5,441,517 A | 8/1995 | Kensey et al. |
| 5,449,375 A | 9/1995 | Vidal et al. |
| 5,456,693 A | 10/1995 | Conston et al. |
| 5,467,780 A | 11/1995 | Nabai et al. |
| 5,478,337 A | 12/1995 | Okamoto et al. |
| 5,486,359 A | 1/1996 | Caplan et al. |
| 5,514,097 A | 5/1996 | Knauer |
| 5,514,158 A | 5/1996 | Kanesaka |
| 5,522,840 A | 6/1996 | Krajicek |
| 5,531,759 A | 7/1996 | Kensey et al. |
| 5,533,518 A | 7/1996 | Vogler |
| 5,545,178 A | 8/1996 | Kensey et al. |
| 5,550,127 A | 8/1996 | Pantano |
| 5,571,181 A | 11/1996 | Li |
| 5,578,459 A | 11/1996 | Gordon et al. |
| 5,584,827 A | 12/1996 | Korteweg et al. |
| 5,591,204 A | 1/1997 | Janzen et al. |
| 5,635,387 A | 6/1997 | Fei et al. |
| 5,643,317 A | 7/1997 | Pavcnik et al. |
| 5,653,387 A | 8/1997 | Takayanagi et al. |
| 5,653,694 A | 8/1997 | Powles |
| 5,656,036 A | 8/1997 | Palmaz |
| 5,665,114 A | 9/1997 | Weadock et al. |
| 5,676,689 A | 10/1997 | Kensey et al. |

(Continued)

FOREIGN PATENT DOCUMENTS

| | | |
|---|---|---|
| AU | 2011295954 B2 | 8/2015 |
| AU | 2015252071 A1 | 11/2015 |

(Continued)

OTHER PUBLICATIONS

Chen et al., Effect of DMSO Concentration, Cell Density and Needle Gauge on the Viability of Cryopreserved Cells in Three Dimensional Hyaluronan Hydrogel, Conf Proc IEEE Eng Med Biol Soc., (2013), pp. 1-11.*

(Continued)

*Primary Examiner* — Jennifer M.H. Tichy
(74) *Attorney, Agent, or Firm* — Goodwin Procter LLP

(57) ABSTRACT

Disclosed are viable cell compositions and related methods of preparation, maintenance and use. The viable cell composition can contain specified levels of cells, hydroxyethyl starch, and dimethylsulfoxide, and can be cryopreserved. The cryopreserved form of the composition can be thawed and combined with an aqueous liquid diluting medium to prepare a diluted viable cell composition that can contain specified, reduced levels of the dimethylsulfoxide and hydroxyethyl starch. The diluting medium can contain trehalose. The prepared, diluted viable cell composition can be administered to a patient.

20 Claims, No Drawings

(56)        References Cited

U.S. PATENT DOCUMENTS

| | | | |
|---|---|---|---|
| 5,681,334 A | 10/1997 | Evans et al. |
| 5,701,910 A | 12/1997 | Powles |
| 5,707,393 A | 1/1998 | Kensey et al. |
| 5,709,934 A | 1/1998 | Bell et al. |
| 5,716,375 A | 2/1998 | Fowler |
| 5,725,498 A | 3/1998 | Janzen et al. |
| 5,741,223 A | 4/1998 | Janzen et al. |
| 5,746,724 A | 5/1998 | Powles et al. |
| 5,752,974 A | 5/1998 | Rhee et al. |
| 5,789,147 A | 8/1998 | Rubenstein et al. |
| 5,827,199 A | 10/1998 | Alexander |
| 5,827,735 A | 10/1998 | Young et al. |
| 5,830,130 A | 11/1998 | Janzen et al. |
| 5,837,539 A | 11/1998 | Caplan |
| 5,861,004 A | 1/1999 | Kensey et al. |
| 5,902,280 A | 5/1999 | Powles et al. |
| 5,916,265 A | 6/1999 | Hu |
| 5,928,214 A | 7/1999 | Rubenstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,955,110 A | 9/1999 | Patel et al. |
| 6,007,563 A | 12/1999 | Nash et al. |
| 6,045,569 A | 4/2000 | Kensey et al. |
| 6,090,130 A | 7/2000 | Nash et al. |
| 6,090,996 A | 7/2000 | Li |
| 6,096,052 A | 8/2000 | Callister et al. |
| 6,096,080 A | 8/2000 | Nicholson et al. |
| 6,126,675 A | 10/2000 | Shchervinsky et al. |
| 6,145,688 A | 11/2000 | Smith |
| 6,179,863 B1 | 1/2001 | Kensey et al. |
| 6,183,496 B1 | 2/2001 | Urbanski |
| 6,190,353 B1 | 2/2001 | Makower et al. |
| 6,200,336 B1 | 3/2001 | Pavcnik et al. |
| 6,206,907 B1 | 3/2001 | Marino et al. |
| 6,206,931 B1 | 3/2001 | Cook et al. |
| 6,245,090 B1 | 6/2001 | Gilson et al. |
| 6,245,527 B1 | 6/2001 | Busfield et al. |
| 6,261,309 B1 | 7/2001 | Urbanski |
| 6,277,140 B2 | 8/2001 | Ginn et al. |
| 6,299,619 B1 | 10/2001 | Greene, Jr. et al. |
| 6,312,474 B1 | 11/2001 | Francis et al. |
| 6,358,284 B1 | 3/2002 | Feamot et al. |
| 6,432,116 B1 | 8/2002 | Callister et al. |
| 6,432,119 B1 | 8/2002 | Callister et al. |
| 6,440,373 B1 | 8/2002 | Gomes |
| 6,482,179 B1 | 11/2002 | Chu et al. |
| 6,537,257 B1 | 3/2003 | Wien |
| 6,537,807 B1 | 3/2003 | Smith et al. |
| 6,540,735 B1 | 4/2003 | Ashby et al. |
| 6,569,081 B1 | 5/2003 | Nielsen et al. |
| 6,659,338 B1 | 12/2003 | Dittman |
| 6,777,231 B1 | 8/2004 | Katz et al. |
| 6,852,533 B1 | 2/2005 | Rafii et al. |
| 6,979,307 B2 | 12/2005 | Beretta et al. |
| 7,029,666 B2 | 4/2006 | Bruder et al. |
| 7,052,907 B2 | 5/2006 | Shi et al. |
| 7,060,494 B2 | 6/2006 | Bhat |
| 7,153,324 B2 | 12/2006 | Case et al. |
| 7,166,133 B2 | 1/2007 | Evans et al. |
| 7,175,652 B2 | 2/2007 | Cook et al. |
| 7,176,022 B2 * | 2/2007 | Frey ..................... A01N 1/0221 |
| | | 435/325 |
| 7,201,848 B2 | 4/2007 | Antwilder et al. |
| 7,255,879 B2 | 8/2007 | Hariri |
| 7,311,904 B2 | 12/2007 | Hariri |
| 7,311,905 B2 | 12/2007 | Hariri |
| 7,387,216 B1 | 6/2008 | Smith |
| 7,456,024 B2 | 11/2008 | Dahm et al. |
| 7,468,276 B2 | 12/2008 | Hariri |
| 7,470,537 B2 | 12/2008 | Laughlin et al. |
| 7,470,538 B2 | 12/2008 | Laughlin et al. |
| 7,556,801 B2 | 7/2009 | Wernet |
| 7,560,280 B2 | 7/2009 | Wernet |
| 7,674,434 B2 | 3/2010 | Sakal et al. |
| 7,745,106 B2 | 6/2010 | Grippi et al. |
| 7,886,779 B2 | 2/2011 | Smith |
| 7,914,779 B2 | 3/2011 | Hariri |
| 7,955,850 B2 | 6/2011 | Yu et al. |
| 7,993,918 B2 | 8/2011 | Paludan et al. |
| 8,517,957 B2 | 8/2013 | Decaluwe et al. |
| 8,652,802 B2 | 2/2014 | Rutty |
| 8,709,797 B2 | 4/2014 | Woods |
| 8,763,287 B2 | 7/2014 | Hilpert |
| 9,029,138 B2 | 5/2015 | Groelz |
| 9,549,715 B2 | 1/2017 | Woods et al. |
| 9,554,557 B2 | 1/2017 | Nehls |
| 10,653,397 B2 | 5/2020 | Woods et al. |
| 2001/0041900 A1 | 11/2001 | Callister et al. |
| 2001/0045765 A1 | 11/2001 | Nelson |
| 2002/0038111 A1 | 3/2002 | Alchas et al. |
| 2002/0064519 A1 | 5/2002 | Bruder et al. |
| 2002/0169408 A1 | 11/2002 | Beretta et al. |
| 2003/0028172 A1 | 2/2003 | Epstien et al. |
| 2003/0109832 A1 | 6/2003 | Rindlisbacher |
| 2004/0019295 A1 | 1/2004 | Zhou et al. |
| 2004/0071786 A1 | 4/2004 | Grippi et al. |
| 2004/0087998 A1 | 5/2004 | Lee et al. |
| 2005/0013844 A1 | 1/2005 | Hadlock et al. |
| 2005/0049626 A1 | 3/2005 | Burgard |
| 2005/0163750 A1 | 7/2005 | Roser et al. |
| 2005/0209568 A1 | 9/2005 | Shanley |
| 2005/0228310 A1 | 10/2005 | Pfistershammer |
| 2005/0239897 A1 | 10/2005 | Pittenger et al. |
| 2006/0134596 A1 | 6/2006 | Sjogren et al. |
| 2006/0182724 A1 | 8/2006 | Riordan |
| 2006/0210544 A1 | 9/2006 | Honmou et al. |
| 2006/0245977 A1 | 11/2006 | Bodner |
| 2007/0009490 A1 | 1/2007 | Conte et al. |
| 2007/0021684 A1 | 1/2007 | Brielmeier et al. |
| 2007/0036767 A1 | 2/2007 | Mistry et al. |
| 2007/0148106 A1 | 6/2007 | Wertz et al. |
| 2007/0178071 A1 | 8/2007 | Westenfelder |
| 2007/0178591 A1 | 8/2007 | Honmou et al. |
| 2007/0270710 A1 | 11/2007 | Frass et al. |
| 2008/0027477 A1 | 1/2008 | Obermiller |
| 2008/0044313 A1 | 2/2008 | Caisley |
| 2008/0095749 A1 | 4/2008 | Aggarwal et al. |
| 2008/0121050 A1 | 5/2008 | Sakal et al. |
| 2008/0175821 A1 | 7/2008 | Chang et al. |
| 2008/0190857 A1 | 8/2008 | Beretta et al. |
| 2008/0213227 A1 | 9/2008 | Aggarwal et al. |
| 2008/0228163 A1 | 9/2008 | Smith |
| 2008/0241112 A1 | 10/2008 | Westenfelder |
| 2008/0241113 A1 | 10/2008 | Walton et al. |
| 2008/0286246 A1 | 11/2008 | Honmou et al. |
| 2009/0053182 A1 | 2/2009 | Ichim et al. |
| 2009/0112119 A1 | 4/2009 | Kim |
| 2009/0180997 A1 | 7/2009 | Pittenger et al. |
| 2009/0193880 A1 | 8/2009 | Halverson et al. |
| 2009/0208463 A1 | 8/2009 | Pittenger et al. |
| 2009/0214484 A1 | 8/2009 | Mironov |
| 2009/0214485 A1 | 8/2009 | Gavrilova et al. |
| 2009/0220464 A1 | 9/2009 | Aggarwal et al. |
| 2009/0246181 A1 | 10/2009 | Kuroda et al. |
| 2009/0269311 A1 | 10/2009 | Lee et al. |
| 2010/0040588 A1 | 2/2010 | Walton et al. |
| 2010/0068191 A1 | 3/2010 | Danilkovich et al. |
| 2010/0098672 A1 | 4/2010 | Varney et al. |
| 2010/0201791 A1 | 8/2010 | Slvenburg et al. |
| 2010/0248215 A1 | 9/2010 | Halverson et al. |
| 2010/0255484 A1 | 10/2010 | Halverson et al. |
| 2010/0280414 A1 | 11/2010 | Haywood et al. |
| 2010/0297094 A1 | 11/2010 | Harlan et al. |
| 2010/0323027 A1 | 12/2010 | Lim et al. |
| 2010/0330047 A1 | 12/2010 | Valorani |
| 2011/0027238 A1 | 2/2011 | Aggarwal et al. |
| 2011/0123498 A1 | 5/2011 | Westenfelder |
| 2011/0129447 A1 | 6/2011 | Meretzki et al. |
| 2011/0142807 A1 | 6/2011 | Pittenger et al. |
| 2011/0212002 A1 | 9/2011 | Curry et al. |
| 2011/0256111 A1 | 10/2011 | Camussi et al. |
| 2011/0262402 A1 | 10/2011 | Kuroda et al. |
| 2011/0275955 A1 | 11/2011 | Lee et al. |

(56)                    References Cited

U.S. PATENT DOCUMENTS

| | | |
|---|---|---|
| 2011/0282240 A1 | 11/2011 | Al Mohizea |
| 2011/0305673 A1 | 12/2011 | Spees |
| 2012/0010526 A1 | 1/2012 | Hilpert et al. |
| 2012/0027730 A1 | 2/2012 | Delgado et al. |
| 2012/0037563 A1 | 2/2012 | Liao |
| 2012/0052049 A1 | 3/2012 | Woods et al. |
| 2012/0128641 A1 | 5/2012 | Austen, Jr. |
| 2012/0149108 A1 | 6/2012 | Tanabe et al. |
| 2012/0201791 A1 | 8/2012 | Yoo |
| 2012/0269785 A1 | 10/2012 | Woods et al. |
| 2012/0269786 A1 | 10/2012 | Woods et al. |
| 2012/0269787 A1 | 10/2012 | Woods et al. |
| 2013/0164267 A1 | 6/2013 | Lin et al. |
| 2015/0272993 A1 | 10/2015 | Strober et al. |
| 2016/0089401 A1 | 3/2016 | Woods et al. |
| 2017/0014454 A1 | 1/2017 | Woods et al. |
| 2017/0332623 A1 | 11/2017 | Zacharias et al. |
| 2017/0336400 A1 | 11/2017 | Meng et al. |
| 2021/0252155 A1 | 8/2021 | Woods et al. |

FOREIGN PATENT DOCUMENTS

| | | |
|---|---|---|
| AU | 2017/241626 A1 | 11/2018 |
| AU | 2015/339886 B2 | 5/2019 |
| BR | 112017006533 A2 | 12/2017 |
| BR | 112018070084 A2 | 2/2019 |
| CN | 1156967 A | 8/1997 |
| CN | 1786154 A | 6/2006 |
| CN | 103180435 A | 6/2013 |
| CN | 107106488 A | 8/2017 |
| CN | 109195445 A | 1/2019 |
| DE | 2903760 B1 | 6/1980 |
| DE | 10144127 C1 | 2/2003 |
| EP | 0917879 A2 | 5/1999 |
| EP | 1876233 A1 | 1/2008 |
| EP | 2191835 A1 | 2/2010 |
| EP | 2105498 A1 | 5/2012 |
| EP | 2721930 A1 | 4/2014 |
| FR | 2522959 A1 | 9/1983 |
| JP | H10-192364 | 7/1998 |
| JP | 2004-507454 A | 3/2004 |
| JP | 2008-544957 A | 12/2008 |
| JP | 2009-242265 | 10/2009 |
| JP | 2011-001114 | 1/2011 |
| JP | 2012-500021 A | 1/2012 |
| JP | 2013-233102 A | 11/2013 |
| JP | 2017-531446 A | 10/2017 |
| JP | 2019-510042 A | 4/2019 |
| RU | 2180529 C2 | 3/2002 |
| SU | 1673130 A1 | 8/1991 |
| SU | 1690737 A1 | 11/1991 |
| SU | 1718837 A1 | 3/1992 |
| WO | WO 1987/00062 A1 | 1/1987 |
| WO | WO 1992/06639 A2 | 2/1993 |
| WO | WO 1994/26175 A1 | 11/1994 |
| WO | WO 95/33488 A1 | 12/1995 |
| WO | WO 1997/19643 A2 | 6/1997 |
| WO | WO 1998/22158 A2 | 5/1998 |
| WO | WO 1998/25545 A1 | 6/1998 |
| WO | WO 2000/13624 A2 | 3/2000 |
| WO | WO 2000/32112 A1 | 6/2000 |
| WO | WO 2000/32250 A1 | 6/2000 |
| WO | WO 2000/32253 A1 | 6/2000 |
| WO | WO 2000/72759 A2 | 12/2000 |
| WO | WO 2000/74576 A1 | 12/2000 |
| WO | WO 2001/045765 A1 | 6/2001 |
| WO | WO 2001/080865 A2 | 11/2001 |
| WO | WO 2005/020823 A1 | 3/2005 |
| WO | WO 2005/030035 A2 | 4/2005 |
| WO | WO 2005/045008 A1 | 5/2005 |
| WO | WO 2005/070302 A1 | 8/2005 |
| WO | WO 2006/078034 A1 | 7/2006 |
| WO | WO 2006/079205 A1 | 8/2006 |
| WO | WO 2006/119256 A2 | 11/2006 |
| WO | WO 2006/121445 A2 | 11/2006 |
| WO | WO 2006/123699 A1 | 11/2006 |
| WO | WO 2007/002260 A2 | 1/2007 |
| WO | WO 2007/011443 A2 | 1/2007 |
| WO | WO 2007/064819 A2 | 6/2007 |
| WO | WO 2007/077560 A2 | 7/2007 |
| WO | WO 2007/090150 A2 | 8/2007 |
| WO | WO 2007/090155 A1 | 8/2007 |
| WO | WO 2008/020815 A1 | 2/2008 |
| WO | WO 2009/031606 A1 | 3/2009 |
| WO | WO 2010/056341 A2 | 5/2010 |
| WO | WO 2010/057965 A1 | 5/2010 |
| WO | WO 2011/011055 A2 | 1/2011 |
| WO | WO 2011/047345 A2 | 4/2011 |
| WO | WO 2013/023075 A1 | 2/2013 |
| WO | WO 2013/023075 A4 | 2/2013 |
| WO | WO 2016/069173 A2 | 7/2016 |
| WO | WO 2017/172679 A1 | 10/2017 |

OTHER PUBLICATIONS

Di et al. "Development and Evaluation of trehalose Contained soltuon Formula to Preserve huc-MSCs at 4C" Journal of Cellular Physiology 27:879-884, 2012.

Halle et al., Uncontrolled-rate freezing and storae at −80 C, with only 3.5-percent DMSO in cryoprotective solution for 109 autologous peripheral blood progenitor cell transplatations, Transfusion, vol. 41, (May 2001), pp. 667-673.

Maruyama et al., Simplified method for cryopreservation of islets using hydroxyethyl starch and dimethyl sulfoxide as cryoprotectants, Transplantation Proceedings, vol. 36, No. 4 (May 1, 2004), pp. 1133-1134.0041-1345.

Moroff et al., Retention of cellular properties of PBPCs following liquid storage and cryopreservation, Transfusion, vol. 44, 2004, pp. 245-252.

Stiff et al., Autologous bone marrow transplantation using unfractionated cells cryopreserved in dimethylsulfoxide and hydroxyethyl starch without controlled-rate freezing, Blood, vol. 46, No. 2 Oct. 1, 1987, pp. 974-978, [retrieved on May 12, 2017). Retrieved from the Internet.

Stolzing et al., Hydroxyethylstarch in cryopreservation—Mechanisms, benefits and problems, Transfusion and Apheresis Science, vol. 46, No. 2, Apr. 1, 2012, pp. 137-147. 1473-0502.

Thirumala et al., Clinical grade adult stem cell banking, Organogenesis, 5:3, 2009, pp. 143-154.

International Application No. PCT/US2017/024411 International Search Report and Written Opinion, mailed May 12, 2017, 15 pgs.

Barry et al., "Mesenchymal stem cells: clinical applications and biological characterization" International Journal of Biochemistry and Cell Biology 2004, 568-584.

Bonab et al., Aging of mesenchymal stem cells in vitro. BMC Cell Biology 2006, 7:14, pp. 1-7.

Brooke et al., Points to Consider in Designing Mesenchymal Stem Cell-Based Clinical Trials, Transfusion Medicine and Hemotherapy, Jul. 21, 2008, vol. 35, pp. 279-285.

CEH Horse Report, A Publication of the Center for Equine Heath, US Davis School of Veterinary Medicine, Oct. 2008, vol. 26, No. 4 in 16 pages.

Chapter 10, "The Pericardium", Handbook of Pathology and Pathophysiology of Cardiovascular Disease, vol. 240, Springer Netherlands (2002).

Chen et al., "Comparison of the Effects of Different Cryoprotectants on Stem Cells from Umbilical Cord Blood", Stem Cells International, vol. 2016, Jan. 1, 2016 (Jan. 1, 2016), pp. 1-7, XP055665649, us ISSN: 1687-966X, DOI: 10.1155/2016/1396783.

Choi et al., The Role of Mesenchymal Stem Cells in the Functional Improvement of Chronic Renal Failure , Stem Cells and Development, vol. 18, No. 3 (2009), pp. 521-529.

Choi et al., Mesenchymal Stem Cell Therapy for Chronic Renal Failure, (2010) Expert Opinion on Biological Therapy, 10:8, 1217-1226, DOI:10.1517/14712598.2010.500284.

Dissanayaka et al., "Characterization of dental pulp stem cells isolated from canine premolars," J Endod. (Aug. 2011) 37(8):1074-1080.

(56)　　　　References Cited

OTHER PUBLICATIONS

Endoluminal Stenting; Chapter 45, Kenneth R. Kensey; Chapter 46, Artur M Spokojny and Timothy A. Sanborn; and Chapter 48, Nicholas N. Kipshidze, Joseph B. Horn, Victor Nikolaychik and John E. Baker, edited by Ulrich Sigwart; W.B. Saunders 1996.
Garcia-Pineres, Alfonso J. et al., "DNAse treatment following thawing of cryopreserved PBMC is a procedure suitable for lymphocyte functional studies", Journal of Immunological methods, (May 17, 2006), vol. 313, No. 12, pp. 209-213.
Gargett et al., Isolation and Culture of Epithelial Progenitors and Mesenchymal Stem Cells from Human Endometrium. Biology of Reproduction 80, 1136-1145, 2009.
Gonzalez et al., "A putative mesenchymal stem cells population isolated from adult human testes" Biochemical and Biophysical Research Communications 385 (2009) 570-575.
Hall et al., Evaluation of the Potential Use of Adipose-Derived Mesenchymal Stromal Cells in the Treatment of Canine Atopic Dermatitis: A Pilot Study, Veterinary Therapeutics, Summer 2010, vol. 11, No. 2.
Heeschen, C., et al. "Nicotine Stimulates Angiogenesis and Promotes Tumor Growth and Atherosclerosis", Nature Medicine, vol. 7., No. 7, Jul. 2001, pp. 833-839.
Himpson, Rebecca C., et al. "Histological evidence for enhanced anal fistula repair using autologous fibroblasts in a dermal collagen matrix." Comparative Clinical Pathology, Apr. 2006, vol. 16, No. 1.
Information from Vascular Solutions web site (www.vascularsolutions. com) on Duett sealing device; two pages,2001.
Information from Vasoseal web site (www.vasoseal.com) on VasoSeal ES, three pages, 2001.
Information from Vasoseal web site (www.vasoseal.com) on VasoSeal VHD, three pages, 2001.
Information from web site (www.pbm.ct.utwente.nl/dopdrachten/wonder.htm) on Nerve Regeneration, three pages, 2001.
Johnson, C. et al. "Matrix Metalloproteinase-9 is Required for Adequate Angiogenic Revascularization of Ischemic Tissues: Potential Role in Capillary Branching", Circulation Research, vol. 94 (2004) pp. 262-268.
Kee, "Arterial Puncture Site Management", Applied Radiology, Jul. 2000, pp. 7-12.
Khairy, G.E.A. et al., "Percutaneous obliteration of duodenal fistula", J.R. Coll. Surg. Edinb., 45, Oct. 2000, 342-344.
Kharaziha et al., Improvement of liver function in liver cirrhosis patients after autologous mesenchymal stem cell injection: a phase 1-11 clinical trial, European Journal of Gastroenterology & Hepatology (2009), vol. 21, pp. 1199-1205.
Kraitchman et al., Dynamic imaging of Allogenic Mesenchymal Stem Cells Trafficking to Myocardia Infarction, 2005, 112:1451-1461.
Lakota et al., "Autologous stem cell transplantation with stem cells preserved in the presence of 4.5 and 2.2% DMSO", Correspondence, 1996, pp. 262-263.
Lee et al., "A Long-Term Follow-Up Study of Intravenous Autologous Mesenchymal Stem Cell Transplantation in Patients with Ischemic Stroke" Stem Cells Journals, vol. 28, No. 6 (Jun. 2010), pp. 1099-1106.
Lindner et al., Mesenchymal Stem or Stromal Cells: Toward a Better Understanding of Their Biology?, Transfus Med Hemother. [online] Mar. 15, 2010, 37(2): pp. 75-83. [retrieved on Sep. 25, 2018]. Retrieved from the internet <URL: https://www.ncbi.nlm. nih.gov/pmc/articles/PMC2914415/.
Lisle, David A., et al., "Percutaneous Gelfoam Embolication of Chronic Enterocutaneous Fistulas: Report of Three Cases", Diseases of the Colon & Rectum, vol. 50, No. 2, Dec. 2006.
Lu et al., Haematologica 2006; 91:1017-1026), Isolation and characterization of human umbilical cord mesenchymal stem cells with hematopoiesis-supportive function and other potentials [online], 2006 [retrieved on Jun. 21, 2017]. Retrieved from the Internet: <URL: http://www.citationmachine.neU>.

Maluf-Filho, F. et al., "Endoscopic Treatment of Esophagogastric Fistulae with an Acellular Matrix", Gastrointestinal Endoscopy, Elsevier, NL, vol. 59, No. 5, Apr. 2004 (Apr. 2004), p. 151, XP004854594 abstract.
Miklos, J.R., et al., "Rectovaginal Fistula Repair Utilizing a Cadaveric Dermal Allograft", International Urogynecology Journal, 1999, vol. 10, No. 6, pp. 405-406.
Moore et al., "Rectovaginal Fistula Repair Using a Porcine Dermal Graft", Obstetrics & Gynecology, Nov. 2004, vol. 104, No. 5, Part 2, pp. 1165-1167.
Neupane et al., Isolation and Characterization of Canine Adipose-Derived Mesenchymal Stem Cells, Tissue Engineering: Part A, vol. 14, No. 6, 2008.
Part 17: Gastrointestinal Tract, part of the LUMEN Histology Slide Series, http://www.meddean.luc.edu/lumen/MEdEd/Histo/frames/h_fram17.html.
R&D Systems, Stem Cell Culture Products and Protocol Guide, 2008, pp. 1-34.
Rojewski et al., "Phenotypic Characterization of Mesenchymal Stem Cells from Various Tissues" Transfus Med Hemother 2008;35:168-184.
Schultz, David J., et al., "Porcine Small Intestine Submucosa as a Treatment for Enterocutaneous Fistulas", Journal of American College of Surgeons, 2002, vol. 194, No. 4, Apr. 2002, pp. 541-543.
Schwesinger, Wyne H., "Management of Persistent Fistula After Gastrectomy?", online question (www.medscape.com/viewarticle/432411_print), posted on May 14, 2002.
Semenov, et al. "Multipotent Mesenchymal Stem Cells from Human Placenta: Critical Parameters for Isolation and Maintenance of Sternness after Isolation." [online] American Journal of Obstetrics and Gynecology, vol. 202, No. 2, 2010, pp. 193.e1-193.e13 [retrieved on Sep. 25, 2018]. Retrieved from the internet <URL:https://www. ajog.org/article/S0002-9378(09)02007-9/fulltext>.
Shah, A.M. et al., "Bronchoscopic closure of bronchopleural fistula using gelfoam", abstract. Journal of Association of Physicians of India, 2004, vol. 52 No. JUIN, pp. 508-509.
Shaker MA, Hindy AM, Mounir RM, Geaisa KM. Egypt Dent. J. Jul. 1995; 41(3): 1237-42.
Sheiman, Robert G., et al., "Percutaneous Treatment of a Pancreatic Fistula after Pancreaticoduodenectomy", J Vase Interv Radial, 2001, vol. 12, No. 4, pp. 524-526.
Shelton, Andrew A., et al., Transperineal Repair of Persistent Rectovaginal Fistulas Using an Accelular Cadaveric Dermal Grant (AlloDerm). Diseases of the Colon & Rectum, Sep. 2006, Vo .. 49, No. 9.
Silbert et al., "Usefulness of Collagen Plugging with VasoSeal after PTCA as Compared to Manual Compression with Identical Sheath Dwell Times", Catheterization and Cardiovascular Diagnosis, 1998, vol. 43, pp. 421-427.
Thermo Scientific Nalgene and Nunc, Cryopreservation Guide, Jan. 2010, pp. 1-16, 06 .
Wu C F, "Improved cryopreservation of human embryonic stem cells with trehalose". Reproductive BioMedicine Online, Jan. 1, 2005 Elsevier, Amsterdam, NL. vol. 11, No. 6, pp. 733-739.
Zucconi et al., Mesenchymal Stem Cells Derived From Canine Umbilical Cord Vein—A Novel Source for Cell Therapy Studies, Stem Cells and Development, vol. 19, No. 3, 2010.
International Preliminary Report on Patentability in international application No. PCT/US2011/049977, with mailing date of Mar. 5, 2013 in 5 pages.
Office Action in Australian Patent Application No. 2015252071, dated Dec. 23, 2016 in 5 pages.
Office Action in Canadian Patent Application No. 2,809,272, dated Jun. 28, 2019, in 4 pages.
Office Action in Canadian Patent Application No. 2,809,272, dated Jul. 12, 2018, in 4 pages.
Office Action in Canadian Patent Application No. 2,809,272, dated Jun. 20, 2017, in 5 pages.
Office Action in Canadian Patent Application No. 2,809,272, dated Sep. 22, 2020, in 5 pages.
International Search Report of PCT/US2011/049977, dated Jan. 17, 2012 in 3 pages.

(56) References Cited

OTHER PUBLICATIONS

Office Action in European Patent Application No. 11822565.5, dated Dec. 12, 2019, in 10 pages.
Office Action in European Patent Application No. 11822565.5, dated Oct. 8, 2020, in 10 pages.
Office Action in European Patent Application No. 11822565.5, dated Jul. 6, 2021, in 9 pages.
Search Report in Brazilian Application No. BR 11 2013 004917 0, dated May 4, 2020, in 24 pages.
International Preliminary Report on Patentability in international application No. PCT/US2012/050173, with mailing date of Feb. 11, 2014.
International Search report and Written Opinion in International Application No. PCT/US2012/050173, with a mailing date of Nov. 30, 2012.
Communication Pursuant to Article 94(3) EPC in European Application No. 12750939.6, with a mailing date of Jul. 27, 2016, in 5 pages.
Office Action in European Patent Application No. 12750939.6, dated Mar. 18, 2019, in 5 pages.
International Preliminary Report on Patentability in international application No. PCT/US2015/052950, with mailing date of Apr. 4, 2017.
Office Action in Brazilian Patent Application No. BR112017006533-9, dated Jan. 21, 2021, in 12 pages.

Office Action in Brazilian Patent Application No. BR112017006533-9, dated Feb. 2, 2021, in 1 page.
Office Action in Brazilian Patent Application No. BR112017006533-9, dated Mar. 11, 2021, in 8 page.
International Search Report of PCT/US2015/052950, dated May 20, 2016 in 4 pages.
International Search Report of Chinese Patent Application No. 2015800622943, dated Sep. 29, 2015 in 2 pages.
Office Action in Chinese Patent Application No. 2015800622943, dated Sep. 30, 2019, in 11 pages.
Office Action in European Patent Application No. 15854446.0, dated Sep. 2, 2019, in 7 pages.
Office Action in Japanese Patent Application No. 2017-536231, dated Aug. 6, 2019, in 15 pages.
Office Action in Australian Patent Application No. 2017241626, dated Apr. 6, 2021, in 5 pages.
International Preliminary Report on Patentability in international application No. PCT/US2017/024411, with mailing date of Oct. 2, 2018 in 15 pages.
Office Action in European Patent Application No. 17716037.1, dated Feb. 25, 2020, in 17 pages.
Office Action in European Patent Application No. 17716037.1, dated Oct. 8, 2020, in 9 pages.
Office Action in European Patent Application No. 17716037.1, dated Aug. 20, 2021, in 5 pages.

* cited by examiner

VIABLE CELL COMPOSITIONS, AND METHODS RELATED TO SAME

INCORPORATION BY REFERENCE TO ANY PRIORITY APPLICATIONS

The present application is a continuation of and claims the benefit of priority to U.S. patent application Ser. No. 15/471,578, filed Mar. 28, 2017, which claims the benefit of priority to U.S. Provisional Patent App. No. 62/314,316, filed Mar. 28, 2016, each of which is hereby incorporated by reference in its entirety.

BACKGROUND

Aspects of the present disclosure related generally to viable cellular compositions and methods of their preparation, storage and use.

Administration of cellular compositions to humans and animals in the treatment of various pathologies or disorders has become increasingly prevalent and bears hope to improve a multitude of therapies. The ability to stably store viable cells and to then prepare them and deliver them to patients is important. Additives to the compositions for cryopreservation must be effective to preserve viability and also biologically acceptable when ultimately delivered to the patient. As well, to facilitate their broad distribution and use, it is highly beneficial if the compositions can be effectively stored through a range of conditions that are achievable without undue capital or other expense in the manufacturing and/or distribution chain.

In view of the background in the area, there remain needs for improved and/or alternative methods and compositions related to storage-stable cell preparation, and their distribution, storage and ultimate use. Aspects of the present disclosure are addressed to these needs.

SUMMARY

It has been discovered that highly robust, storable, viable cell preparations can be achieved when incorporating controlled concentrations of additives that help to preserve viability during cryopreservation, but which ultimately provide easy access to therapeutic, viable cell compositions for administration to patients. Accordingly, in one aspect, the present disclosure provides a method for making, storing and preparing viable cells that can be administered to a patient. The method includes preparing an unfrozen liquid composition including about 500,000 viable cells/ml to about 20 million viable cells/ml and an aqueous cryopreservation medium including dimethylsulfoxide at a concentration of about 1 to 3% and hydroxyethyl starch at a concentration of about 2% to 10%. The unfrozen liquid composition is sealed in a cryopreservation container. The cryopreservation container is stored in a freezer at a temperature in the range of about –60° C. to –100° C. The cryopreservation container is removed from the freezer and thawed to provide a thawed viable cell composition having viable cells suspended in the aqueous cryopreservation medium. A diluting aqueous liquid medium is combined with the thawed viable cell composition, for example in a volume ratio of at least 5:1, to provide a diluted viable cell composition containing hydroxyethyl starch and dimethylsulfoxide, with the dimethylsulfoxide present in the diluted viable cell composition at a concentration of about 0.5% or less. The diluted viable cell composition can also contain the hydroxyethyl starch at a concentration that can be greater than the concentration of the dimethylsulfoxide and/or that can be at least 0.1%. The diluted viable cell composition can be administered to a patient.

In another aspect, provided is a method for treating a patient with viable cells. The method includes thawing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%, to provide a thawed viable cell composition having the viable cells suspended in an aqueous liquid. The method also includes combining a diluting aqueous liquid medium with the thawed viable cell composition to provide a diluted viable cell composition containing hydroxyethyl starch and dimethylsulfoxide, wherein the dimethylsulfoxide is present in the diluted viable cell composition at a concentration of about 0.5% or less. The method also includes administering the diluted viable cell composition to a patient.

In another aspect, provided is a method for preparing viable cells that can be used to treat a patient. The method includes thawing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%, to provide a thawed viable cell composition having the viable cells suspended in an aqueous liquid. The method also includes combining a diluting aqueous liquid medium with the thawed viable cell composition to provide a diluted viable cell composition containing hydroxyethyl starch and dimethylsulfoxide, wherein the dimethylsulfoxide is present in the diluted viable cell composition at a concentration of about 0.5% or less.

In another aspect, provided is a method for treating a patient with viable cells. The method includes storing a cryopreservation container in a freezer at a temperature in the range of about –60° C. to –100° C., the cryopreservation container containing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%. The cryopreserved composition is thawed to provide a thawed viable cell composition having the viable cells suspended in an aqueous liquid, the aqueous liquid having the dimethylsulfoxide at a concentration of about 1% to 3% and the hydroxyethyl starch at a concentration of about 2% to 10%. A diluting aqueous liquid medium is combined with the thawed viable cell composition to provide a diluted viable cell composition containing hydroxyethyl starch and dimethylsulfoxide, wherein the dimethylsulfoxide is present in the diluted viable cell composition at a concentration of about 0.5% or less. The diluted viable cell composition is administered to a patient.

In a further aspect, provided is a method for treating a patient with viable cells. The method includes administering a viable cell composition to the patient, the viable cell composition containing viable cells suspended in an aqueous liquid containing dimethylsulfoxide at a concentration of 0.5% or less and hydroxyethyl starch at a concentration that can be greater than the concentration of dimethylsulfoxide and/or can be at least 0.1%.

In another aspect, provided is a viable cell product including a cryopreservation container containing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%.

In another aspect, provided is a method for maintaining viable cells. The method includes maintaining in a cryopreserved condition a composition that includes viable cells and an aqueous cryopreservation medium, wherein the cryopreservation medium contains dimethylsulfoxide at a concentration of about 1% to 3% and hydroxyethyl starch at a concentration of about 2% to 10%.

In another aspect, provided is a viable cell composition for administration to a patient. The viable cell composition includes an aqueous medium comprising dimethylsulfoxide at a concentration of less than 0.5%, and hydroxyethyl starch at a concentration that can be greater than that of the dimethylsulfoxide and/or can be at least 0.1%. The cellular composition also includes viable cells suspended in the aqueous medium, preferably at a concentration of about 200,000 cells/ml to about 10 million cells/ml.

In another aspect, provided is a viable cell composition. The composition includes viable cells and an aqueous cryopreservation medium. The aqueous cryopreservation medium contains dimethylsulfoxide at a concentration of about 1% to 3% and hydroxyethyl starch at a concentration of about 2% to 10%. In various embodiments, the composition can be in liquid form or in a cryopreserved condition, for example at a temperature of about −60° C. or lower, for example in some variants at a temperature of about −60° C. to −100° C.

Additional embodiments of the present disclosure, as well as features and advantages thereof, will be apparent from the descriptions herein.

DETAILED DESCRIPTION

Reference to certain embodiments will be made in this detailed description and specific language will be used to describe the embodiments. It will be understood that this description is intended to be illustrative. Any alterations and further modifications in the described embodiments, and any further applications of the principles thereof, are contemplated as would normally occur to one skilled in the art to which this disclosure pertains.

As disclosed above, in certain aspects the present disclosure relates to viable cell compositions and to related methods of preparation, storage and use. In the discussions that follow, a number of potential features or combinations of features are disclosed. It is to be understood that each such disclosed feature or combination of features can be combined with the generalized features discussed in the Summary above, or in the List of Certain Disclosed Embodiments below, to form a disclosed embodiment of the present invention. In addition, all percentages given herein are given as percentage by weight, unless otherwise stated.

A wide variety of cell types may be used in embodiments of the present disclosure. For example, the cells can be skin cells, skeletal muscle cells, cardiac muscle cells, lung cells, mesentery cells, adipose cells, or stem cells such as mesenchymal stem cells. Adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

When used, mesenchymal stem cells (MSC) can be obtained from any suitable tissue. These include as examples MSCs derived from dental tissue (such as those harvested from dental pulp, periodontal ligaments, or other dental tissues), testicle tissue, bone marrow; peripheral blood, placental tissue, uterine tissue (including endometrial regenerative cells), umbilical cord blood, umbilical cord tissue, or skin tissue (including full thickness skin tissue). These or other MSCs can be used in aspects of the present disclosure. The MSCs can be generally an adherent cell population expressing markers CD90 and CD105 (>90%) and lacking expression of CD34 and CD45 and MHC class II (<5%) as detected by flow cytometry.

The cells used in the embodiments herein can be from any suitable species of animal, for example a mammal, such as a human, canine (e.g. dog), feline (e.g. cat), equine (e.g. horse), porcine, ovine, caprine, or bovine mammal.

The cells, in a viable state, will be combined with an aqueous cryopreservation medium that includes dimethylsulfoxide (DMSO) and a carbohydrate which in preferred embodiments is hydroxyethyl starch (HES). HES and DMSO are readily available commercially. The combination of the cells with the DMSO and HES can be conducted in any suitable fashion, including by combining the viable cells with a solution containing both DMSO and HES, or by combining the cells with separate solutions, one of which contains the DMSO and another of which contains the HES. These and other modes of providing the viable cells in the aqueous cryopreservation medium will be suitable. As well, it will be understood that the cryopreservation medium can contain agents other than the DMSO and HES, including other cryopreservation agents. However, in preferred forms, the DMSO and HES will constitute at least 50%, at least 70%, at least 80%, at least 90%, essentially all (98% or more) or all of the cryopreservation medium other than the water.

In preferred prepared viable cell compositions to be cryopreserved, the cryopreservation medium will include the DMSO at a concentration of about 5% or less or about 3% or less, and most preferably in the range of about 1% to 3% or in the range of about 1.5% to about 2.5%; and, will include the HES at a concentration of about 12% or less or about 10% or less, and most preferably in the range of about 2% to 10% or in the range of about 4% to about 8%. In certain preferred forms, the cryopreservation medium includes DMSO at a concentration of about 2% and HES at a concentration of about 6%.

In preferred prepared viable cell compositions to be cryopreserved, the viable cells will be present at a concentration of at least about 200,000 cells/ml, at least about 500,000 cells/ml, at least about 1 million cells/ml, at least about 5 million cells/ml, or at least about 10 million cells/ml; and/or the viable cells will be present at a concentration not exceeding about 50 million cells/ml, not exceeding about 30 million cells/ml, or not exceeding about 20 million cells/ml. In certain variants, the viable cells will be present in the cell composition at a concentration in the range of about 500,000 to about 20 million cells/ml, or in the range of about 3 million to about 20 million cells/ml, or in the range of about 5 million to about 15 million cells/ml, or in the range of about 8 million to about 12 million cells/ml. In some forms, the viable cells will be present in the viable cell composition at a concentration of about 10 million cells/ml.

The viable cell composition including the viable cells and the above-disclosed cryopreservation medium, in unfrozen (liquid) form, can be prepared in, delivered into, or otherwise provided in a cryopreservation container such as a cryopreservation vial or cryopreservation bag. In preferred forms, the cell composition is provided in a cryopreservation vial having features as disclosed in U.S. Pat. No. 8,709,797 issued Apr. 29, 2014, which is hereby incorporated by reference. Preferred cryopreservation vials will thus include an access port, preferably a needle septum, through which the viable cells can be sterilely accessed with a needle or other cannulated device after a period of storage (e.g. in cryopreserved state) in the vial. The preferred vials will also include two additional ports to the interior of the vial, which can be used as filling and vent ports (the vent port preferably containing a sterile filter). These two additional ports can be fitted with heat sealable tubing, which can be heat sealed to seal the vial after filling, and which can thereafter be cut prior to accessing the cells in the vial, for example to provide a vent for needle-based removal of the cell composition through the needle septum. In preferred forms, each cryopreservation container will contain about 1 ml to about 10 ml of the cell composition, more preferably about 1 ml to about 5 ml of the composition, and most preferably about 2 ml to about 3 ml of the composition. Preferred cryopreservation vials for use in embodiments herein are commercially available as CellSeal® Cryogenic Vials (Cook Regentec LLC, Bloomington, IN).

The cryopreservation container containing the viable cell composition can be subjected to cryopreservation conditions to cause the composition to be cryopreserved. For example, the cryopreservation conditions can include storing the cryopreservation container at a temperature at which the viable cell composition freezes. For example, the cell composition can be maintained in a cryopreserved state at a temperature in the range of about −60° C. or lower, for example in the range of about −60° C. to −150° C., more preferably about −60° C. to −100° C., and even more preferably about −70° C. to −90° C. In certain forms, the cell composition can be maintained in a cryopreserved state at a temperature of about −80° C.±5° C. In most preferred forms, the cryopreservation container is stored in a mechanical freezer (a freezer, typically electrically-powered, that uses a re-circulating refrigerant within an air cooler that exchanges heat from air circulating within the freezer to reduce the temperature of contents within the freezer) to maintain the cell composition in a cryopreserved state at the stated temperatures. Advantageously, this avoids the need to use liquid nitrogen tanks for cryopreservation storage, at least during a storage phase when the mechanical freezer is used (e.g. a mechanical freezer in operation at a point of care location to which the viable cell composition is shipped, stored in the mechanical freezer, thawed and then used, e.g. to treat a patient). Thus, in some embodiments, the cryopreservation container containing the viable cell composition can be stored under cryopreservation conditions (e g immersed in liquid nitrogen and/or in a mechanical freezer as disclosed herein) at the manufacturing facility, a distribution facility, or another facility that is a distance from a point of care facility, the cryopreservation container containing the viable cells can be shipped to the point of care while maintaining cryopreservation conditions (e.g. in a shipping package containing a liquid nitrogen system and/or dry ice—frozen carbon dioxide), and the cryopreservation container containing the viable cells can be stored at the point of care (e.g. a veterinary clinic or hospital) under cryopreservation conditions until needed for administration, preferably within a mechanical freezer as disclosed herein.

Preferred viable cell compositions containing the cells, HES and DMSO exhibit good capacity to maintain the viability of the cells during storage at a temperature in the range of about −60° C. to −100° C. For example, preferred compositions will lose no more than 20% of their initial viable cells, no more than 10% of their viable cells, or no more than 5% of their viable cells, when stored at a temperature in the range of −60° C. to −100° C. for a period of six months, and more preferably when stored at a temperature in the range of −60° C. to −100° C. for a period of one year. Such storage stabilities under the relatively moderate cooling conditions enable advantageous product distribution and use methods in which multiple point of care locations (e.g. 10 or more, or 20 or more locations) can maintain mechanical freezers in which a plurality of cryopreservation containers each containing a cell composition as described herein are stored. The stability of the viability of the cells under these storage conditions can provide an acceptable shelf life at the point of care. Immediately prior to administration (e.g. within 6 hours, or within 2 hours, or within 1 hour), a cryopreservation container can be removed from the freezer and the composition therein thawed for additional manipulation (e.g. dilution as described below) and/or administration.

In some methods herein, to thaw the cell composition, the cryopreservation container can be caused to warm to a temperature at which the frozen cell composition reverts to a liquid form. This can be achieved in any suitable manner. For example, the container, remaining sterilely sealed, can be exposed to a gaseous environment (e.g. the room air environment at the point of care) at room temperature (e.g. about 20° C. to 25° C.) to thaw the cell composition. In another form, the container can be incubated in a heated liquid bath to thaw the cell composition, for example heated to a temperature in the range of about 33° C. to 37° C., preferably about 37° C. The cryopreservation and subsequent thawing of the cell composition will preferably result in high maintenance of cell viability, for example with the thawed composition retaining at least 80%, at least 90%, or at least 95% of the viable cells of the initial cell composition prior to cryopreservation.

After thawing, the viable cell composition can be removed from the cryopreservation container. For example, in some embodiments, the cryopreservation container has a septum through which a needle or other cannulated device may be passed to access the container contents, while maintaining a sterile environment within the container. The needle or other cannulated device can then be used to withdraw the cell composition from the container sterilely, for example into a syringe barrel or other vessel. It will be understood that other methods for accessing the cell composition within and removing the viable cell composition from the cryopreservation container may be used in other embodiments.

In some forms, the viable cell composition can be administered to a patient, or put to a research or other use, unmodified from its composition upon removal from the cryopreservation container. In some embodiments, the viable cell composition is modified for use, including for use in administration to a patient. The modification can include, for example, the addition of one or more substances to the viable cell composition.

In preferred methods, the viable cell composition is combined with an aqueous liquid diluting medium to dilute the cell concentration of the composition, and potentially also dilute the concentration of other components, such as HES and/or DMSO, of the viable cell composition. In beneficial aspects, the diluting aqueous liquid medium can be a physiologically acceptable aqueous liquid, such as a phosphate-buffered or otherwise buffered saline solution, potentially with other additives. Also, it will be understood that the diluting aqueous liquid medium can be combined with the viable cell composition as a single volume of a given composition, or as multiple volumes of the same composition or of differing compositions.

In preferred methods, to prepare a diluted viable cell composition for administration to a patient or other use, a diluting aqueous liquid medium will be combined with the cell composition in a volume ratio of at least 2:1, at least 3:1, at least 5:1, or at least 8:1. In more preferred forms, such volume ratio will be in the range of about 3:1 to about 20:1, or about 5:1 to about 15:1. It is contemplated that the cell concentration, DMSO concentration and HES concentration in the prepared diluted composition will be correspondingly reduced relative to the starting cell composition prior to dilution; however, in some forms the diluting aqueous liquid medium may itself contain some concentration of cells, HES and/or DMSO, albeit typically lower than the concentration in the starting cell composition so as to result in some dilution of cells, HES and DMSO in the diluted cell composition.

The combination of the thawed cell composition with the diluting aqueous liquid medium can be conducted in any suitable container or vessel. In beneficial modes, the combination is conducted in a second container (other than the cryopreservation or other container in which the cells were stored or held). This second container can include an input port or other input member, for example a septum, for sterile transfer of materials such as the cell composition and/or the diluting aqueous liquid medium into the second container. In some forms, combining the cell composition and diluting aqueous liquid medium can include delivering both of these into the second container, for example in either order or simultaneously. In other forms, the second container can be provided as a pre-manufactured container already containing the diluting aqueous liquid medium in sterile condition, and the cell composition can be added to the pre-manufactured container. In any of these embodiments, the second container can be a bag and/or can have an outlet port spaced from the input port or other member for delivery of the prepared diluted cell composition from the bag or other container, e.g. for delivery into a patient. The second container can be a bag having a septum for sterile input of materials and a valved port for outlet of materials, e.g. as occurs in common saline bags for patient treatment in medical care. The thawed cell composition, and potentially the trehalose-containing medium (if not pre-manufactured in the bag) can be sterilely delivered into the bag by needle through the septum, and the prepared diluted cell composition can be sterilely delivered to a patient through the valved port.

In certain embodiments, the diluting aqueous liquid medium will be combined with the viable cell composition, and the prepared diluted cell composition will have a DMSO concentration that has been reduced from its initial level (e.g. any of those levels indicated above for the cryopreserved cell composition) to a diluted concentration of about 0.5% or less, more preferably about 0.3% or less, and in some embodiments to a diluted concentration in the range of about 0.05% to about 0.5% or in the range of about 0.1% to about 0.3%. In addition or alternatively, the diluting aqueous liquid medium will be combined with the cell composition, and the prepared diluted cell composition will have an HES concentration that is greater than that of the DMSO and/or which is at least about 0.1%, more preferably at least about 0.3%, and in some embodiments a concentration in the range of about 0.1% to about 6% or in the range of about 0.3% to about 2%. HES (at 6% concentration) is a known volume extender for administration to the bloodstream, and thus it is contemplated that the diluting aqueous liquid medium can in some embodiments contain significant levels of HES while nonetheless preparing a diluted cell composition well suited for administration to the bloodstream of a human or other animal patient. Thus in some modes of operation, the diluted composition can have a DMSO concentration that is reduced to a greater extent than the reduction, if any, of the HES concentration, as compared to the starting cell composition prior to dilution. In regard to the cell concentration in the diluted cell composition, the diluting aqueous liquid medium will typically not contain any cells, and the cell concentration of the diluted viable cell composition will the lower than that of the starting cell composition, for example in the range of about 100,000 cells/ml to about 20 million cells/ml, or about 250,000 cells/ml to about 5 million cells/ml, or about 500,000 cells/ml to about 2 million cells/ml. In certain forms, the cell concentration of the prepared diluted cell composition will be about 1 million cells/ml.

In certain embodiments herein, the diluting aqueous liquid medium will contain trehalose. Trehalose, also known as mycose or tremalose, is an alpha-linked disaccharide formed by an $\alpha,\alpha$-1,1-glucoside bond between two $\alpha$-glucose units. It has a chemical name of (2R,3S,4S,5R,6R)-2-(hydroxymethyl)-6-[(2R,3R,4S,5S,6R)-3,4,5-trihydroxy-6-(hydroxymethyl)oxan-2-yl]oxyoxane-3,4,5-triol (IUPAC naming convention). The diluting aqueous liquid medium can contain any suitable concentration of trehalose for these purposes. In certain aspects, the diluting aqueous liquid medium will contain trehalose at a concentration of about 1% to about 20% by weight, or about 1% to about 10% by weight, or about 2% to about 7% by weight, or about 2.5% to about 5% by weight, or about 3% to about 4% by weight. The diluting aqueous liquid medium, whether it contains trehalose as specified herein or not, can also include other components and/or have a specified osmolarity. For example, it can include sodium chloride at a physiologically acceptable level, for example at a level in the range of about 0.5% to about 1.5%, e.g. about 0.9% (isotonic). The diluting aqueous liquid medium can also include a buffer, for example phosphate buffer, and can have a pH in the range of about 6 to 8, or about 6.8 to 7.8, or about 7 to 7.5. The diluting aqueous liquid medium can also have an osmolarity in the range of 200 to 600 milliosmols per kilogram (mosm/kg), or 250 to 500 mosm/kg, or 250 to 400 mosm/kg.

A diluting aqueous liquid medium containing trehalose can be combined with the cell composition containing DMSO and HES, to prepare a trehalose-containing diluted cell composition having a suitable concentration of trehalose, along with HES and DMSO (e.g. with the HES and DMSO in the concentrations for the diluted cell composition specified above). This concentration of trehalose in the prepared diluted viable cell composition, in certain embodiments, is in the range of about 1% to about 10% by weight trehalose or about 2% to about 7% by weight, or about 2.5% to about 5% by weight, or about 3% to about 4% by weight. Additionally or alternatively, the concentration of trehalose can be effective to inhibit clumping of the cells as compared to a corresponding cell composition without the trehalose. Inhibition of clumping can be observed by the formation of fewer and/or smaller clumps of cells in the prepared cell composition, for example at a time point at least ten minutes after preparation of the cell composition, at least twenty minutes after preparation of the cell composition, or at least after 60 minutes after preparation of the cell composition. The capacity of the trehalose to inhibit clumping for significant periods of time following preparation of the cell composition can, for example, provide sufficient time to administer the prepared cell composition to a patient, for example by injecting or infusing the cell composition into the bloodstream of a patient by venous or arterial access and/or by local implantation of the cell composition. In therapeutic applications of cell compositions, the composition can be administered to the patient over a relatively prolonged period of time, for example at least 10 minutes, at least 20 minutes, or at least 60 minutes.

As disclosed herein, the prepared diluted viable cell composition can have specified concentrations of cells, DMSO, HES and/or trehalose. Where minimum or maximum concentrations, or ranges of concentrations, are stated, it will be understood that the conditions of the dilution of the starting viable cell composition can be controlled to achieve the stated amounts in the prepared diluted viable cell composition. These conditions include, for example, the concentrations of components in the starting viable cell composition prior to dilution, the volume ratio of the diluting aqueous liquid medium used relative to the starting viable cell composition, and the concentrations (if any) of the identified components in the diluting aqueous liquid medium.

The prepared diluted cell composition can be put to any suitable use, including for example research or therapeutic uses. For therapeutic use, the cell composition may as examples be administered to a human or animal patient to treat or prevent a disease or condition such as degenerative bone disease, osteoarthritis, rheumatoid arthritis, polyarthritis, systemic lupus erythematosus, inflammatory bowel disease, atopy, hepatitis, chronic steroid responsive meningitis-arteritis, beagle pain syndrome, degenerative myelopathy, chronic renal failure disease, dilated and mitral cardiomyopathy, keratoconjunctivitis sicca, immune mediated non-erosive arthritis, immune mediated hemolytic anemia, immune mediated thrombocytopenia, Evans syndrome, intervertebral disc disease, muscle fibrosis secondary to disease or trauma, refractory conical ulcer, diabetes mellitus, spinal trauma, eosinophilic granuloma complex, hypertrophic cardiomyopathy, cholangitis, spinal injury, exercise induced pulmonary hemorrhage, rhabdomyolysis, conical ulcer, eczema, multiple sclerosis, muscular dystrophy, spinal injury, diabetes mellitus, hepatitis, myocardial infarction, congestive heart failure, or muscle fibrosis.

The prepared diluted cell composition can be administered to a patient in any suitable manner. In certain forms, the cell composition is delivered systemically into the bloodstream of a patient, for example by delivery into a vein or artery. In other forms, the cell composition is delivered topically to the patient (e.g. in the treatment of atopy or other skin disorders). In still other forms, the cell composition is delivered to a local implant site in a patient. Any of these or any combination of these modes of administration may be used in the treatment of a patient. In certain combination treatments, a first amount of a prepared cell composition herein can be delivered systemically into the bloodstream of a patient, and a second amount of a prepared cell composition herein (e.g. prepared with or separately from the first amount and including the same type(s) or a different type(s) of cells) is implanted locally in or near one or more skeletal joints in a patient to treat an arthritic condition, e.g. any of those arthritic conditions identified herein. Also, in patient treatments herein, a single administration of a prepared cell composition as described herein can be made in some embodiments, while in others multiple separate administrations of prepared cell compositions as described herein may be made over time (e.g. weekly or monthly administrations). In further embodiments, the prepared, diluted cell composition can be filtered prior to administration to the patient, e.g. to remove any clumps of cells that may be present. In certain forms, the cell composition can be passed through an in-line filter positioned in tubing through which the cell composition is passed into the bloodstream of the patient, e.g. into a vein or artery of the patient. Such a filter can, in certain variants, have a particle size cutoff of about 200 micrometers (i.e. exclude from passage particles having a maximum cross-sectional dimension of greater than about 200 micrometers) or lower, or a particle size cutoff of about 170 micrometers or lower, or a particle size cutoff of about 100 micrometers or lower, while allowing the passage of singly suspended cells through the filter.

Additional embodiments herein include products useful in preparing diluted cell compositions as described herein. In one embodiment, provided is a diluting aqueous liquid medium useful for preparing a diluted cell composition. The diluting aqueous liquid medium can contain those components, and in amounts, as specified herein. As well, the diluting aqueous liquid medium can be provided in sterile form in a container that is included in a kit. That container may be a vial, bag or other container. In certain forms, the container has the features of the "second container" discussed hereinabove in which the diluted cell composition can be prepared, including for example having an inlet port or other member (e.g. needle septum) and a separate outlet port as discussed above. Kits disclosed herein may include the container containing the diluting aqueous liquid medium along with one or more additional components, for example including but not limited to a liquid transfer device such as a syringe and attached or attachable needle, and potentially also a container containing the starting cell composition to be used to prepare the diluted cell composition. The container containing the starting cell composition can include the cell composition in a cryopreserved state (e.g. shipped frozen with the kit) or in a non-cryopreserved (e.g. thawed where the cells were previously cryopreserved) state, including embodiments in which the cryopreserved cell composition contains HES and DMSO in any of those amounts therefor specified above. Kits disclosed herein may also include at least one filter, for example a filter as described above, through which a prepared diluted cell composition can be passed prior to administration into a patient, and/or tubing through which the diluted cell composition can be passed during administration to a patient.

The following specific Experimental is provided to facilitate a further understanding of aspects of the present disclosure. It will be understood that this Experimental is illustrative, and not limiting, in nature.

Example 1

C-URCs Isolation and Culture

Fully intact uteri are obtained from a local low-cost spay-neuter clinic from female canines that have presented for ovariohysterectomy. Once the samples arrive at the laboratory, the ovaries are removed and discarded then the uterus separated into approximate one gram, full thickness sections.

A one gram sample is then minced to ≤1 mm³ fragments using a sterile scalpel. The chopped tissue is placed into an enzymatic bath and digested for 30 min at 37° C. Once digestion is complete, the enzymes are neutralized with culture media (DMEM-HG with 10% fetal bovine serum and 0.25 mg/mL amphotericin B, 100 IU/mL penicillin-G, and 100 mg/mL streptomycin), centrifuged at 300×g for 5 min and re-suspended in fresh culture media. The contents are then strained through a 200 μm sterile membrane and plated in a 25 cm² flask. After 14 days of culture, the cells are split as Passage 0 (P0) using TrypZean™ solution and cell counts and viability are assessed using a standard trypan blue dye exclusion assay and hematocytometer. The resulting cells are termed canine uterine regenerative cells (C-URCs).

Example 2

C-URCs Cryopreservation, Thawing, and Dilution

C-URC's prepared as in Example 1, or prepared by expanding a culture prepared as in Example 1 in a bioreactor, are suspended at a concentration of 10 million cells/ml in a cryopreservation solution containing 2% DMSO and 6% HES, and this cell composition is sterilely filled in 3 ml aliquots into respective cryopreservation vials (available as 5 ml capacity CellSeal® Cryogenic Vials from Cook Regentec LLC, Bloomington, IN). The vials are sealed and then frozen and stored at −80° C. in a mechanical freezer for one to twelve months.

After its storage period, a vial is removed from the freezer and thawed by immersing the vial in a 37° C. water bath for several minutes. After thawing, the sterile filter-containing vent tube of the vial is cut to open the vent, and a sterile syringe needle is used to penetrate the needle septum of the vial and withdraw the cell composition into the syringe barrel. The needle is then removed from the vial's septum, and used to penetrate the septum input port of a sterile bag containing 27 ml of a buffered physiologic saline solution containing 3.67% trehalose. The prepared, diluted cell composition has a cell concentration of 1 million cells/ml, and DMSO, HES and trehalose concentrations of 0.2%, 0.6% and 3.3%, respectively. The prepared diluted cell composition can be administered to a patient from a valved output port of the bag, for example through medical tubing having an in-line filter to remove clumped cells. The administration can be intravenous.

LIST OF CERTAIN DISCLOSED EMBODIMENTS

The following provides an enumerated, non-limiting listing of certain embodiments that are disclosed herein.

Embodiment 1

A method for treating a patient with viable cells, comprising:
thawing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%, to provide a thawed viable cell composition having the viable cells suspended in an aqueous liquid;
combining an aqueous liquid diluting medium with the thawed viable cell composition, preferably in a volume ratio of at least 2:1 and more preferably at least 5:1, to provide a diluted viable cell composition containing hydroxyethyl starch and dimethylsulfoxide, wherein the dimethylsulfoxide is present in the diluted viable cell composition at a concentration of about 0.5% or less; and
administering the diluted viable cell composition to a patient.

Embodiment 2

A method for preparing viable cells for treating a patient, comprising:
thawing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%, to provide a thawed viable cell composition having the viable cells suspended in an aqueous liquid; and
combining an aqueous liquid diluting medium with the thawed viable cell composition, preferably in a volume ratio of at least 2:1 and more preferably at least 5:1, to provide a diluted viable cell composition containing hydroxyethyl starch and dimethylsulfoxide, wherein the dimethylsulfoxide is present in the diluted viable cell composition at a concentration of about 0.5% or less.

Embodiment 3

The method of embodiment 1 or 2, also comprising, prior to the thawing:
storing a cryopreservation container in a freezer at a temperature in the range of about −60° C. to −100° C., the cryopreservation container containing the cryopreserved composition.

Embodiment 4

The method of any one of the preceding embodiments, wherein the thawed viable cell composition has a concentration of the viable cells in the range of about 1 million cells/ml to about 20 million cells/ml, and wherein the diluted viable cell composition has a concentration of the viable cells in the range of about 200,000 cells/ml to about 5 million cells/ml.

Embodiment 5

The method of any one of the preceding embodiments, also comprising administering the diluted viable cell composition to a patient by delivering the diluted viable cell composition into a blood vessel of the patient.

Embodiment 6

The method of any one of the preceding embodiments, wherein the cryopreservation medium of the cryopreserved composition contains the dimethylsulfoxide at a concentration of about 1.5% to 2.5%.

Embodiment 7

The method of any one of the preceding embodiments, wherein said volume ratio is at least 8:1, and wherein the dimethylsulfoxide is present in the diluted viable cell composition at a concentration of about 0.3% or less.

Embodiment 8

The method of any one of the preceding embodiments, wherein the cryopreservation medium of the cryopreserved composition contains the dimethylsulfoxide at a concentration of about 1.75% to 2.25%.

Embodiment 9

The method of any one of the preceding embodiments, wherein the viable cells comprise viable mesenchymal stem cells.

Embodiment 10

The method of embodiment 9, wherein the viable cells comprise viable canine mesenchymal stem cells.

Embodiment 11

The method of embodiment 9, wherein the viable cells comprise viable feline mesenchymal stem cells.

Embodiment 12

The method of embodiment 9, wherein the viable cells comprise viable equine mesenchymal stem cells.

Embodiment 13

The method of embodiment 9, wherein the viable cells comprise viable human mesenchymal stem cells.

Embodiment 14

The method of any preceding embodiment, wherein the viable cells are derived from dental tissue, testicle tissue, bone marrow; peripheral blood, placental tissue, uterine tissue, umbilical cord blood, umbilical cord tissue, or skin tissue.

Embodiment 15

The method of any preceding embodiment, wherein the diluted viable cell composition contains the hydroxyethyl starch at a concentration of at least about 0.1%, and more preferably at least about 0.3%.

Embodiment 16

The method of any preceding embodiment, wherein the diluted viable cell composition contains the DMSO at a concentration in the range of about 0.05% to about 0.5% and the hydroxyethyl starch at a concentration in the range of about 0.1% to about 6%.

Embodiment 17

The method of any preceding embodiment, wherein the aqueous liquid diluting medium comprises trehalose.

Embodiment 18

The method of embodiment 17, wherein the trehalose is present in the aqueous liquid diluting medium at a concentration of about 1% to about 10%.

Embodiment 19

The method of embodiment 17 or 18, wherein the trehalose is present in the diluted viable cell composition at a concentration of about 2% to about 7%.

Embodiment 20

The method of any one of the preceding embodiments, wherein the cryopreserved composition contains the dimethylsulfoxide at a concentration of about 2% and the hydroxyethyl starch at a concentration of about 6%.

Embodiment 21

A method for maintaining viable cells, comprising:
maintaining in a cryopreserved condition a composition that includes viable cells and an aqueous cryopreservation medium, wherein the cryopreservation medium contains dimethylsulfoxide at a concentration of about 1% to 3% and hydroxyethyl starch at a concentration of about 2% to 10%.

Embodiment 22

The method of embodiment 21, wherein said maintaining comprises maintaining the composition at a temperature in the range of about –60° C. to –100° C.

Embodiment 23

The method of embodiment 21 or 22, wherein said maintaining comprises cooling the composition in a mechanical freezer.

Embodiment 24

The method of any one of embodiment 21 to 23, wherein the composition has a concentration of the viable cells in the range of about 1 million cells/ml to about 20 million cells/ml.

Embodiment 25

The method of any one of embodiments 21 to 24, wherein the cryopreservation medium of the composition contains the dimethylsulfoxide at a concentration of about 1.5% to 2.5%.

Embodiment 26

The method of any one of embodiments 21 to 25, wherein the cryopreservation medium of the composition contains the dimethylsulfoxide at a concentration of about 1.75% to 2.25%.

Embodiment 27

The method of any one of embodiments 21 to 26, wherein the viable cells comprise viable mesenchymal stem cells.

Embodiment 28

The method of any one of embodiments 21 to 27, wherein the viable cells are derived from dental tissue, testicle tissue, bone marrow; peripheral blood, placental tissue, uterine tissue, umbilical cord blood, umbilical cord tissue, or skin tissue.

Embodiment 29

The method of any one of embodiments 21 to 28, wherein the composition contains the dimethylsulfoxide at a concentration of about 2% and the hydroxyethyl starch at a concentration of about 6%.

Embodiment 30

A method for treating a patient with viable cells, comprising:
administering a viable cell composition to the patient, the viable cell composition containing viable cells suspended in an aqueous liquid containing dimethylsulfoxide at a concentration of 0.5% or less and hydroxyethyl starch at a concentration that is greater than that of the dimethylsulfoxide and that is at least 0.1%.

Embodiment 31

The method of embodiment 30, wherein said administering comprises delivering the viable cell composition into a blood vessel of the patient.

Embodiment 32

The method of embodiment 30 or 31, wherein the viable cells comprise viable mesenchymal stem cells.

Embodiment 33

The method of any one of embodiments 30 to 32, wherein the patient is a feline, canine, equine or human patient.

Embodiment 34

The method of any one of embodiments 30 to 33, wherein the viable cell composition also comprises trehalose.

Embodiment 35

The method of embodiment 34, wherein the trehalose is present in the viable cell composition at a concentration of about 2% to about 7%.

Embodiment 36

The method of any one of embodiments 30 to 35, also comprising, prior to said administering, preparing the viable cell composition by combining an aqueous liquid diluting medium with a starting viable cell composition containing dimethylsulfoxide at a concentration of about 1 to 3% and hydroxyethyl starch at a concentration of about 2 to 10%.

Embodiment 37

The method of embodiment 36, wherein said combining is conducted with the aqueous liquid diluting medium and starting viable cell composition in a volume ratio of at least 5:1.

Embodiment 38

The method of embodiment 36 or 37, wherein the aqueous liquid diluting medium comprises trehalose.

Embodiment 39

A product, comprising:
a cryopreservation container containing a cryopreserved composition that includes viable cells and an aqueous cryopreservation medium, wherein the cryopreservation medium of the cryopreserved composition contains dimethylsulfoxide at a concentration of about 1% to 3% and hydroxyethyl starch at a concentration of about 2% to 10%.

Embodiment 40

The product of embodiment 39, wherein the cryopreserved composition is at a temperature in the range of about −60° C. to −100° C.

Embodiment 41

The product of embodiment 39 or 40, also comprising:
a mechanical freezer in which the cryopreservation container is received.

Embodiment 42

The product of embodiment 41, wherein a plurality of said products are received in the mechanical freezer.

Embodiment 43

A viable cell composition for administration to a patient, comprising:
an aqueous medium comprising dimethylsulfoxide at a concentration of less than 0.5%, hydroxyethyl starch at a concentration of at least about 0.1%; and
viable cells suspended in the aqueous medium at a concentration of about 200,000 cells/ml to about 20 million cells/ml.

Embodiment 44

The viable cell composition of embodiment 43, wherein: the aqueous medium also comprises trehalose.

Embodiment 45

The viable cell composition of embodiment 43 or 44, wherein the viable cells are suspended in the aqueous medium at a concentration of about 200,000 cells/ml to about 5 million cells/ml.

Embodiment 46

The viable cell composition of any one of embodiments 43 to 45, wherein the viable cells comprise viable mesenchymal stem cells.

Embodiment 47

The viable cell composition of embodiment 46, wherein greater than 90% of the viable cells express markers CD90 and CD105 and wherein less than 5% of the viable cells express markers CD34, CD45 and MHC class II.

What is claimed is:

1. A method for treating a patient with viable uterine regenerative cells, comprising:

thawing a cryopreserved composition comprising viable uterine regenerative cells and a saline cryopreservation medium, wherein the saline cryopreservation medium of the cryopreserved composition consists of dimethylsulfoxide at a concentration of 2% and hydroxyethyl starch at a concentration of about 2% to about 10% producing a thawed viable uterine regenerative cell suspension;

combining an aqueous liquid diluting medium with the thawed viable uterine regenerative cell suspension in a volume ratio of at least 3:1 to produce a diluted viable uterine regenerative cell composition containing hydroxyethyl starch and dimethylsulfoxide, wherein the dimethylsulfoxide is present in the diluted viable uterine regenerative cell composition at a concentration of about 0.5% or less; and administering the diluted viable uterine regenerative cell composition intravenously to the patient.

2. The method of claim 1, wherein the saline cryopreservation medium of the cryopreserved composition consists of dimethylsulfoxide at a concentration of 2% and hydroxyethyl starch at a concentration of about 4% to about 8%.

3. The method of claim 1, wherein the saline cryopreservation medium of the cryopreserved composition consists of dimethylsulfoxide at a concentration of 2% and hydroxyethyl starch at a concentration of about 6%.

4. The method of claim 1, wherein the viable uterine regenerative cells are viable human uterine regenerative cells.

5. The method of claim 1, wherein the viable uterine regenerative cells are viable canine uterine regenerative cells.

6. The method of claim 1, wherein the viable uterine regenerative cells are viable feline uterine regenerative cells.

7. The method of claim 1, further comprising, prior to thawing the cryopreserved composition, storing the cryopreserved composition at a temperature in the range of about −60° C. to about −100° C.

8. The method of claim 1, wherein the cryopreserved composition comprises viable uterine regenerative cells at a concentration of 10 million cells/mL.

9. The method of claim 1, wherein the patient is being treated for osteoarthritis.

10. The method of claim 1, wherein the patient is being treated for chronic renal failure disease.

11. The method of claim 1, wherein the patient is being treated for eczema.

12. The method of claim 1, wherein the patient is being treated for rheumatoid arthritis.

13. The method of claim 1, wherein the patient is being treated for polyarthritis.

14. The method of claim 1, wherein the patient is a human.

15. The method of claim 1, wherein the patient is a canine.

16. The method of claim 1, wherein the patient is a feline.

17. The method of claim 1, wherein the saline cryopreservation medium is a buffered saline solution.

18. The method of claim 1, wherein the saline cryopreservation medium is a phosphate buffered saline solution.

19. The method of claim 1, wherein the dimethylsulfoxide is present in the diluted viable uterine regenerative cell composition at a concentration of about 0.2%.

20. The method of claim 1, wherein the volume ratio of the aqueous liquid diluting medium to the thawed viable uterine regenerative cell suspension is 8:1.

* * * * *